United States Patent [19]

Michael et al.

[11] Patent Number: 4,709,699
[45] Date of Patent: Dec. 1, 1987

[54] SURGEON'S GIGLI SAW AND METHOD

[75] Inventors: Mark S. Michael, Garrett; Scott A. Glaze, Ft. Wayne, both of Ind.

[73] Assignee: Fort Wayne Metals Research Products Corporation, Fort Wayne, Ind.

[21] Appl. No.: 893,876

[22] Filed: Aug. 6, 1986

[51] Int. Cl.⁴ ............................................. A61B 17/14
[52] U.S. Cl. ....................................... 128/317; 125/18; 125/21; 76/25 R; 76/112
[58] Field of Search .................. 128/317, 305; 125/18, 125/21; 76/25 R, 101 R, 112

[56] References Cited

U.S. PATENT DOCUMENTS

| | | |
|---|---|---|
| Re. 24,660 | 6/1959 | Dessureau et al. |
| 152,970 | 7/1984 | Chase . |
| 1,306,636 | 6/1919 | Selby . |
| 1,543,195 | 6/1925 | Thygesen ............................. 128/317 |
| 1,687,089 | 10/1928 | Green ..................................... 125/18 |
| 2,101,583 | 12/1937 | Honneknovel . |
| 2,123,619 | 7/1938 | Wienholz . |
| 2,156,652 | 5/1939 | Harris ..................................... 125/21 |
| 2,749,949 | 6/1956 | De La Tramerye . |
| 2,988,118 | 6/1961 | De La Tramerye . |
| 3,150,470 | 9/1964 | Barron . |
| 3,257,792 | 6/1966 | Joy . |
| 3,495,590 | 2/1970 | Zeiller . |
| 4,015,931 | 4/1977 | Thakur . |
| 4,580,545 | 4/1966 | Dorsten . |

*Primary Examiner*—John D. Yasko
*Assistant Examiner*—Gene B. Kartchner
*Attorney, Agent, or Firm*—Pearne, Gordon, McCoy & Granger

[57] ABSTRACT

A Gigli saw used by a surgeon to cut bones is constructed of a plurality of round wires which have been deformed in a coining stand so that they form one polygonal shape which in the preferred embodiment is square. This square strand is then twisted along its own axis in a given direction of lay. It is then heat-treated for stress relief and a plurality, such as three, of such strands are twisted together to form a cable. This results in a Gigli saw blade with many cutting edges formed at the edges of the polygon as each such edge is presented at the periphery of the cable. Preferably, the strands have a different number of twists from that of the cable, and are twisted in the opposite direction so that the cutting edges lie at about 5 to 15 degrees relative to the longitudinal axis of the cable. The foregoing abstract is merely a resume of one general application, is not a complete discussion of all principles of operation or applications, and is not to be construed as a limitation on the scope of the claimed subject matter.

27 Claims, 11 Drawing Figures

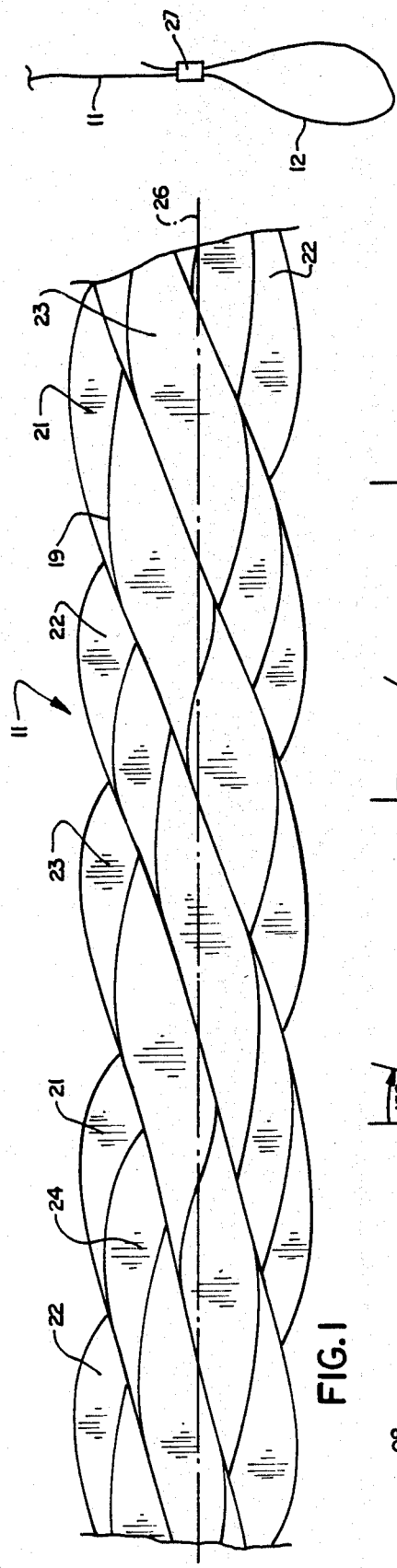
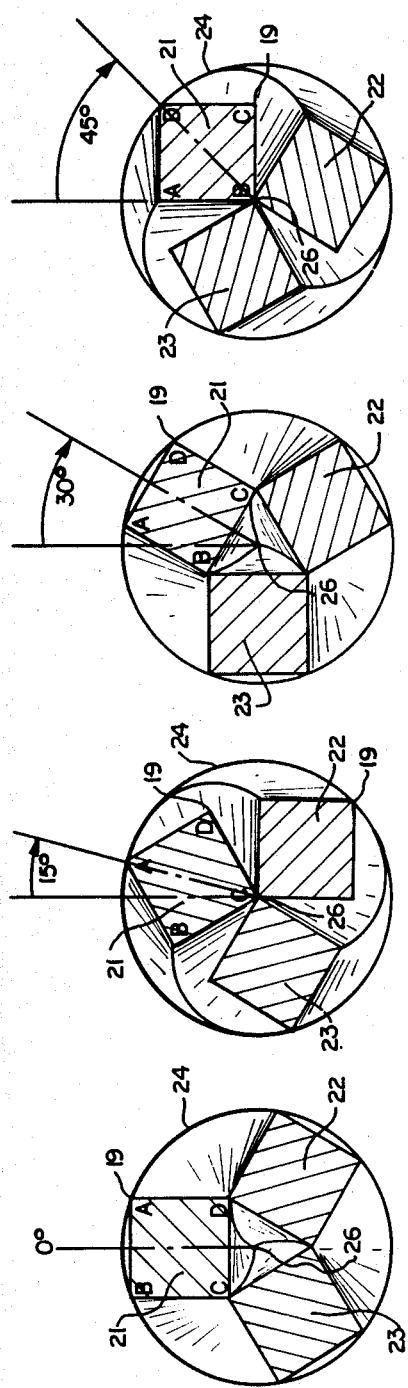
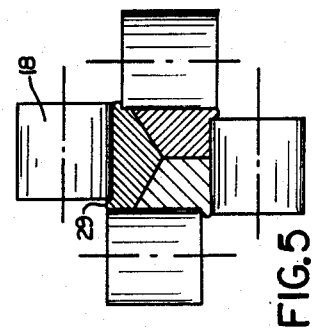
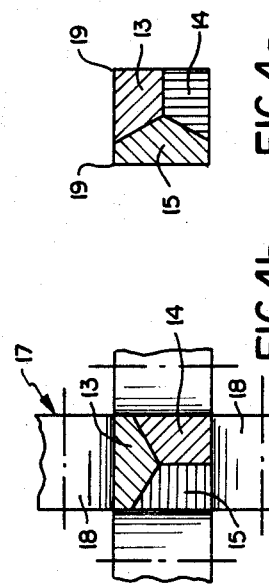
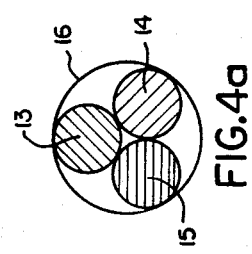

SURGEON'S GIGLI SAW AND METHOD

BACKGROUND OF THE INVENTION

Saw blades made of wire or cable have been used for many years in the stone cutting industry in the shaping of quarried blocks of marble and granite. U.S. Pat. No. 1,306,636 taught the use of a wire cable with one strand projecting slightly beyond the surface of the cable, and being an abrasive cord.

U.S. Pat. No. 2,123,619 suggested the use of three triangular wires in a cable or three rectangular wires, with the apices retained together as the three wires were twisted into a cable so as to provide a maximum space between the wires for containing the abrasive slurry used to perform much of the stone cutting.

U.S. Pat. No. Re. 24,660 suggested the use of two wires twisted into a cable, with each wire being a half-round and a half-square cross section in order to have large interstices for the slurry. U.S. Pat. No. 3,150,470 suggested a braided wire cable with diamond particles embedded thereon. U.S. Pat. No. 4,015,931 suggested a plurality such as seven wires deformed into a circular shape and then with protruding, bonded abrasive particles on the cable. U.S. Pat. No. 4,580,545 suggested the use of two square wires twisted into a cable in a single helical direction, and with the two wires having opposite twists relative to each other.

U.S. Pat. No. 3,257,792 disclosed a two-wire cable, with each wire deformed from a round shape into a generally elliptical shape.

Other objects besides stones have been cut by a twisted wire cable. A type of wood-cutting endless loop band saw was suggested in U.S. Pat. No. 152,970 wherein teeth were cut on one edge of a narrow bar of steel and then the bar twisted so that the teeth were in a spiral around the completed blade. A similar construction for a non-continous loop was disclosed in U.S. Pat. Nos. 2,988,118 and 2,749,949. A relatively stiff saw blade with a handle at one end but with a somewhat similar construction was suggested in U.S. Pat. No. 2,101,583.

U.S. Pat. No. 1,543,195 suggested a type of medical saw blade with four piano wires first twisted in pairs in one direction, the two pairs being then twisted together in the opposite direction.

U.S. Pat. No. 3,495,590 disclosed another type of medical saw for removing casts and had a single wire on which was formed a helical projecting tooth.

A surgeon's Gigli saw is a flexible cable which may be inserted into a person or animal through an opening in the flesh and wrapped around a bone, then pulled alternately on opposite ends to abrasively cut through the bone. Such a saw has a considerably different structure, operation, and result from the stone cutting saws. In the stone cutting saws, one finds a continuous loop cable which travels at high speed, e.g., 4500 feet per minute, and moves only unidirectionally. A typical construction is to reverse the direction of twist of the wires in the cable periodically, e.g., every 50 feet, so as to keep the kerf of the cut in the stone block as nearly planar as possible. Further, such stone cutting wire cables do not have much flex considering their diameter because they travel over large diameter pulleys and there is not much flex at the area of cutting on the block of stone. Further, such wire cables cut primarily by the use of a slurry of silicon carbide or the like, so such cables need large interstices to carry the slurry into the kerf. Also, where such wire cables have pockets to receive abrasive particles bonded to the cable, such pockets materially weaken the wire cable.

The surgeon's Gigli saw, on the other hand, is one which needs to be of much smaller cable, and is bent at about a 180-degree bend around the bone to be cut, so it must be quite flexible. Also, such saws must have high tensile strength so that they will not break during the surgery, either from excessive tensile force or poor flexion capabilities. The saws must also have the proper cutting rate because if the cutting rate is too slow, the operation will take too long and also the surgeon may get too tired before the bone is severed. If the cutting rate is too high, the saw may jam in the kerf and it may be broken by the surgeon in trying to pull it loose. Further, the Gigli saw should have a uniform diameter so that there is a smooth cut and the saw will not bind in the kerf. Accordingly, it is desired to have a saw with a maximum amount of material removal per stroke, and also a saw which will cut equally well in each direction of the stroke. The saw must have good fatigue life so that the bone may be cut using only a single Gigli saw rather than using two or three in succession. The saw need not have extended life, however, because they are discarded after one use, since the saw teeth contain bits of flesh and bone and it is impractical to try to clean and sterilize them.

Accordingly, the problem to be solved is how to construct a surgeon's Gigli saw which will produce a smooth cut, not bind in the kerf, have a maximum amount of material removal per stroke, and have good tension, flexion, and cutting properties.

This problem is solved by a surgeon's Gigli saw comprising, in combination, a cable comprising a plurality of strands twisted together in a first rotational direction, at least one strand of said cable having been previously twisted along its own axis in the opposite rotational direction from that of said cable, and each strand comprising a plurality of wires substantially coined together into a generally polygonal cross-sectional shape.

The problem is further solved by the method of manufacture of a surgeon's Gigli saw comprising the steps of providing a plurality of individual wires, passing said plurality of wires as a bundle through a coining stand to form a strand of said wires substantially coined into a polygonal cross-sectional shape, twisting at least one of said strands in a first rotational direction, providing a plurality of such strands, and twisting said plurality of strands in the opposite rotational direction into a cable.

Accordingly, an object of the invention is to provide a Gigli saw with improved tension, flexion, and cutting characteristics.

Another object of the invention is to provide a Gigli saw with a substantially uniform diameter to obtain a smooth cut and prevent binding in the kerf.

Still another object of the invention is to provide a method of making a Gigli saw which is simple and economical so that the saws may economically be discarded after one use.

A further object of the invention is to provide a Gigli saw with a plurality of substantially square strands twisted into a cable and each strand being coined into a polygonal shape from a plurality of wires.

Other objects and a fuller understanding of the invention may be had by referring to the following description and claims, taken in conjunction with the accompanying drawing.

BRIEF DESCRIPTION OF THE DRAWING

FIG. 1 is an enlarged plan view of a portion of the Gigli saw of the invention;

FIG. 2 is a plan view of an end of the Gigli saw;

FIGS. 3a-3d show successive enlarged cross sections of the saw blade of FIG. 1;

FIGS. 4a-4d show enlarged progressive stages in the formation of a single twisted strand used in the cable of FIG. 1; and FIG. 5 shows an alternative arrangement to FIG. 4b.

DESCRIPTION OF THE PREFERRED EMBODIMENTS

FIG. 1 illustrates a surgeon's Gigli saw 11 constructed according to the present invention. This saw blade may be of a length desired by the surgeon, e.g., 10, 15, or 20 inches long, with a loop 12 at each end through which the surgeon passes a handle (not shown), one at each end in order to alternately pull the saw back and forth while looped around a bone, and hence to cut through the bone.

FIG. 4 shows a preferred process of manufacturing the saw blade 11, and three stainless steel wires 13, 14, and 15 are twisted into a strand 16 and have a generally triangular shape in cross section as shown in FIG. 4a. These three wires are then run through a coining stand to change the shape into a polygonal shape. FIG. 4b shows diagrammatically this coining stand as being a Turk's-head 17, with four rollers 18 acting on the twisted strand of FIG. 4A to deform such strand into substantially a square cross section. The three individual wires 13, 14, and 15 may still be seen if the coined strand is cut and etched, although preferably the Turk's-head sufficiently deforms the wires so as to achieve relatively sharp edges 19, as shown in FIG. 4c. The fact that the strand 16 of FIG. 4a is twisted results in the coined strand also twisting, as shown in the transition from FIG. 4b to 4c.

Next, the square strand of FIG. 4c is twisted along its own axis 20 to form a twisted strand 21, as shown in FIG. 4d. This twist is in a first rotational direction, e.g., clockwise.

Next, a plurality of such twisted strands 21, 22, and 23 are twisted together to form a cable such as is shown in FIG. 3a. This twisting is preferably made in the opposite rotational direction, e.g., counterclockwise. The result is the cable 24 shown in FIG. 1 and shown in successive cross sections in FIGS. 3a-3d. The four corners of strand 21 in FIG. 3 have been labeled A, B, C, and D, in order to better illustrate the progressive twist. Part of the sharp edges 19 become cutting edges as they are presented at the periphery of the cable. These cutting edges are continuously changed along the length of the cable due to the twisting of the individual strands 21-23. In the preferred embodiment, the twisting of the strands relative to the twist of the cable is such that the individual cutting edges extend at about an angle of 5 to 15 degrees relative to the axis 26 of the cable. As shown in FIG. 1, the cutting edges 19 in one of the better examples extended at about a 10-degree angle to this cable axis 26, and extended in a helical lay opposite to the helical lay of the strands 21-23 in the cable 11. The fact that the individual strands are twisted about twice as much as the cable results in the cutting edges 19 lying at an acute angle relative to the cable axis 26, which is of opposite lay to that of the strands in the cable. In other words, if the cutting edges are right hand lay, the strands have a left hand lay.

The cable 24 is next stress-relieved by generally conventional means, e.g., a heat treat at about 1500° F. for about 10 minutes. This improves the flexibility of the cable without materially decreasing the tensile strength. Since the Gigli saw is one which is subjected to rather sharp bends around a bone to be cut, good flexion characteristics are required. After the stress relief, the loops 12 are formed on the ends of a cut section of the wire, and this length of the saw might be from 10 to 20 inches in length as completed with the loops 12. These loops may be secured by a Hulvey splice which is a tube 27 compressed upon the main cable and the end of the cable which is looped back through this tube. The tube may be made of the same material as the cable, e.g., 304 or 316 stainless steel.

Table A shows a number of different tests of slightly different Gigli saws, all with three wires formed into a polygon which is a rectangle, or practically square. This Table shows different tests with either three or four strands formed into the cable, and with different strand twists per inch and cable twists per inch, in most cases, with the strand twisting being opposite to that of the cable twist. The column giving the number of strokes indicates the number of strokes which the Gigli saw was capable of making without failure until one or more bones were cut, and the column indicating the area per stroke indicates the total area cut divided by the number of strokes. Test No. 9 had a relatively large area per stroke for good cutting action, namely a high rate of cutting per stroke. Test No. 2 had a larger number of strokes before the bone was cut through, but had a satisfactory area of removal per stroke. Test No. 10 also had a satisfactory area of removal per stroke, and also had the largest number of strokes before failure, namely, it could cut through four bones. This is the embodiment illustrated in FIGS. 1-4.

TABLE A

| Test No. | Wires | Square | Strands | RH Strand Twist/ Inch | LH Cable Twist/ Inch | Strokes | Area sq. in. Stroke |
|---|---|---|---|---|---|---|---|
| 1 | 3 | .018 × .018 | 4 | 12.5 | 3.25 | 147 | .0289 |
| 2 | 3 | .018 × .018 | 3 | 12.5 | 2.67 | 133 | .0348 |
| 3 | 3 | .018 × .018 | 3 | 12.5 | 4.67 | 157 | .031 |
| 4 | 3 | .019 × .019 | 3 | 16 | 5.5 | 63 | .044 |
| 5 | 3 | .018 × .018 | 3 | 14 | 6 | 197 | .0140 |
| 6 | 3 | .018 × .018 | 3 | 17 | 7.7 | 137 | .0195 |
| 7 | 3 | .018 × .018 | 3 | 0 | 6.5 | 147 | .0187 |
| 8 | 3 | .017 × .017 | 3 | 13 | 6.3 | 137 | .0181 |
| 9 | 3 | .017 × .017 | 3 | 14 | 7.7 | 34 | .084 |
| 10 | 3 | .016 × .016 | 3 | 13 | 7 | 267 | .030 |

FIG. 5 illustrates a further embodiment where the Turk's-head rollers 18 are slightly loosened so that there are extruded ears or edges 29 of about 0.001 inch at the four corners of the polygon. This metal edge then forms a cutting edge which is hardened by being work hardened in passing through the Turk's-head. FIG. 5 illustrates that the polygon of the strands need not be a regular polygon, but may be distorted therefrom.

The Gigli saw of the present invention differs considerably in structure, operation, and use from the prior art saws used for cutting stone. In the stone cutting saws, it was desired to utilize an abrasive slurry to do most of the cutting, and hence the saw wires were ones which had relatively large interstices therebetween in order to carry the slurry into the kerf of the stone. In a Gigli saw, it is certainly not practical to utilize any form of abrasive slurry; instead, the cutting edges 19 perform the cutting as the saw is reciprocated by the surgeon. In the present saw, at least one strand has a different number of twists per inch from that of the cable, and at least one strand has a greater number of twists per inch than the cable. Also, the embodiments disclose a Gigli saw wherein at least one of the strands has been previously twisted along its respective axis, and preferably all three of the strands have been twisted in a direction opposite to the twist of the strands in the cable. The polygonal cross section shown is one which is easily formed, for example, by the Turk's-head roller stand 17, and the polygonal shape in cross section is one which has the exterior faces of the strand meeting at edges with an interior angle not exceeding about 90 degrees.

The stress relief may be performed after all strands are twisted into cable, but is preferably done after the square strand is twisted along its own axis and before the strands are twisted into a cable.

The three wires 13, 14, and 15 preferably each have a diameter of 0.0113 inch as round wire. Also preferably the dimension of the square strand shown in FIG. 4b is about 0.016 inch on each side. This means that the cross-sectional area of the three wires 13–15 has been reduced approximately 20–25% to achieve a good coining of the three wires into the polygonal shape and to assure sharp edges. The excess wire from the reduction in area materializes itself in increased length of the strand. The three wires coined into a generally square strand, and then plural twisted strands in a cable, result in a Gigli saw with many cutting edges, with very good tension, flexion and cutting characteristics.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. A surgeon's Gigli saw comprising, in combination: a cable comprising a plurality of strands twisted together in a first rotational direction; at least one strand of said cable having been previously twisted along its own axis in the opposite rotational direction from that of said cable; and each strand comprising a plurality of wires substantially coined together into a generally polygonal cross-sectional shape.

2. A Gigli saw as set forth in claim 1, wherein said cable comprises at least three strands.

3. A Gigli saw as set forth in claim 1, wherein said at least one strand has a different number of twists per inch from that of said cable.

4. A Gigli saw as set forth in claim 1, wherein said at least one strand has a greater number of twists per inch than said cable.

5. A Gigli saw as set forth in claim 1, wherein at least two of said strands have been previously twisted along their respective axes.

6. A Gigli saw as set forth in claim 1, wherein said polygonal shape of at least one strand is substantially square.

7. A Gigli saw as set forth in claim 1, wherein said polygonal shape of at least one strand has the exterior faces forming the polygonal shape meeting at edges with an interior angle in cross section not exceeding about 90 degrees.

8. A Gigli saw as set forth in claim 1, wherein said at least one strand has about twice the number of twists per inch of said cable.

9. A Gigli saw as set forth in claim 1, wherein each of said strands of said cable has been previously twisted along its respective axis.

10. A Gigli saw as set forth in claim 9, wherein each of said strands of said cable has been previously twisted in said opposite rotational direction from that of said cable.

11. A Gigli saw as set forth in claim 9, wherein each of said polygons is substantially a square.

12. A Gigli saw as set forth in claim 9, wherein each of said strands has about thirteen twists per inch.

13. A Gigli saw as set forth in claim 9, wherein said cable has about seven twists per inch.

14. A Gigli saw as set forth in claim 9, wherein said strands have been twisted to such an extend relative to the opposite twists of the individual strands that the strand edges where adjoining faces meet define cutting teeth extending at about 10 degrees relative to the axis of the cable.

15. A Gigli saw as set forth in claim 1, wherein the twist of said at least one strand relative to the twist of the cable establishes the edges of the polygon of said at least one strand at an angle of about 5 degrees to 15 degrees relative to the longitudinal axis of the cable.

16. The method of manufacture of a surgeon's Gigli saw comprising the steps of:
providing a plurality of individual wires;
passing said plurality of wires as a bundle through a coining stand to form a strand of said wires substantially coined into a polygonal cross-sectional shape;
twisting at least one of said strands in a first rotational direction;
providing a plurality of such strands; and
twisting said plurality of strands in the opposite rotational direction into a cable.

17. The method as set forth in claim 16, wherein said polygonal cross-sectional shape is rectangular.

18. The method as set forth in claim 16, wherein said twisting step includes twisting all of said strands in said first rotational direction.

19. The method as set forth in claim 16, wherein each of said polygonal cross-sectional shapes is substantially square.

20. The method as set forth in claim 16, including providing a sharp edge of not more than about a 90-degree included angle on said polygonal cross-sectional shape.

21. The method as set forth in claim 16, including twisting said bundle of wires prior to passing through said coining stand.

22. The method as set forth in claim 16, wherein the strand twisting step includes twisting together three of said strands.

23. The method as set forth in claim 16, wherein the passing step includes passing said plurality of wires through a Turk's-head roller stand.

24. The method as set forth in claim 23, wherein the passing step includes offsetting the rolls in the Turk's-head roller stand to form projecting ears at the edges of intersecting faces on the sides of the strand.

25. The method as set forth in claim 16, wherein said passing step includes passing three wires through the coining stand.

26. The method as set forth in claim 16, including stress relieving said strands prior to twisting into said cable.

27. The method as set forth in claim 16, wherein said strand twisting step includes twisting the strands into a cable with approximately one-half the number of twists per inch of said at least one of the strands.

* * * * *